United States Patent [19]

Balint, Jr. et al.

[11] Patent Number: 4,865,841

[45] Date of Patent: Sep. 12, 1989

[54] METHODS AND COMPOSITIONS FOR TRANSIENT ELIMINATION OF HUMORAL IMMUNE ANTIBODIES

[75] Inventors: Joseph P. Balint, Jr., Seattle; Sharon Cochran, Edmonds; Frank R. Jones, Edmonds; Harry W. Snyder, Edmonds, all of Wash.

[73] Assignee: Imre Corporation, Seattle, Wash.

[21] Appl. No.: 112,853

[22] Filed: Oct. 23, 1987

[51] Int. Cl.⁴ .................... A61K 39/00; C12N 11/00; G01N 33/552

[52] U.S. Cl. ................................ 424/85.8; 424/85.1; 424/85.2; 424/85.4; 424/85.5; 424/85.6; 424/85.7; 530/387; 436/527; 435/174; 502/400; 502/407; 604/5

[58] Field of Search ............................ 424/85.1–85.8, 424/88; 530/387; 436/527; 435/174; 502/400, 407; 604/5

[56] References Cited

U.S. PATENT DOCUMENTS

| | | | |
|---|---|---|---|
| 4,340,535 | 7/1982 | Voisin et al. | 260/112 |
| 4,576,928 | 3/1986 | Toni et al. | 502/404 |
| 4,590,071 | 5/1986 | Scannon et al. | 424/85 |
| 4,671,958 | 6/1987 | Rodwell et al. | 424/85 |
| 4,681,870 | 7/1987 | Balint, Jr. et al. | 502/403 |

OTHER PUBLICATIONS

Schenkein et al. (1971), J. Clin. Invest. 50:1864.
Terman et al. (1976), Clin. Exp. Immunol. 24:231.
Terman et al. (1976), Clin. Exp. Immunol. 28:130.
Terman et al. (1979), Lancet 2:824.
Balint et al. (1984), Cancer Res. 44:734.
Bensinger et al. (1981), N. Engl. J. Med. 304:160.

Primary Examiner—Margaret Moskowitz
Assistant Examiner—Abdel A. Mohamed
Attorney, Agent, or Firm—Townsend and Townsend

[57] ABSTRACT

Antibody is removed from the blood of patients who are being treated or diagnosed with exogenous macromolecules, such as immunotoxins. As the immunotoxins are foreign antigens, the patient will develop an immune response. The antibodies produced by the immune response upon subsequent immunization with the immunotoxins will interfere with the desired function of the immunotoxins by preventing them from binding with their specific target site. By extracorporeally removing the antibodies, the activity of the immunotoxins can be enhanced.

25 Claims, 3 Drawing Sheets

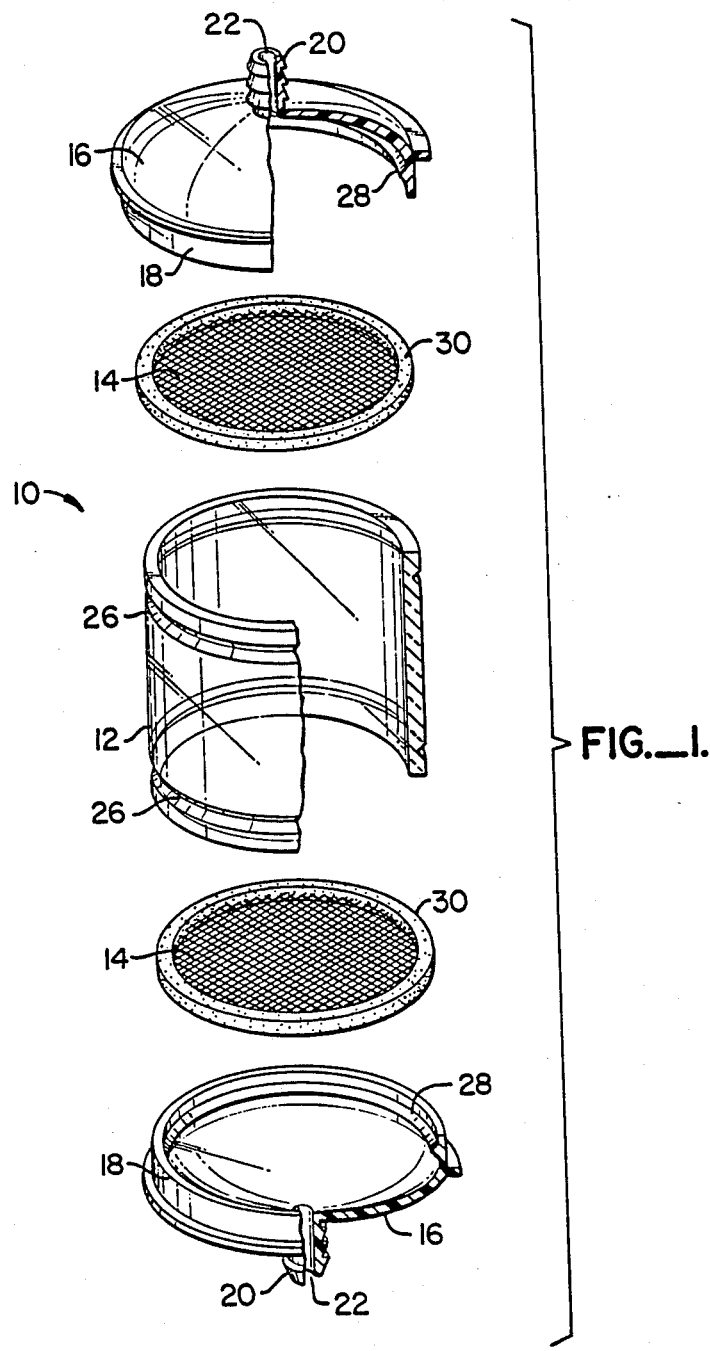
FIG._1.

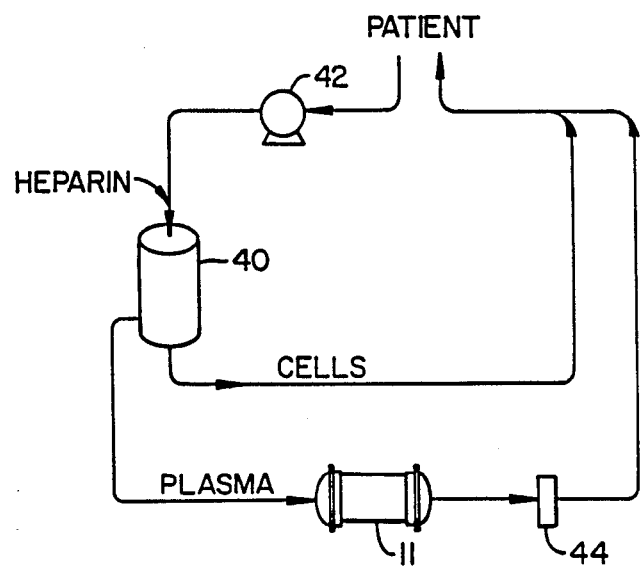
FIG._2.

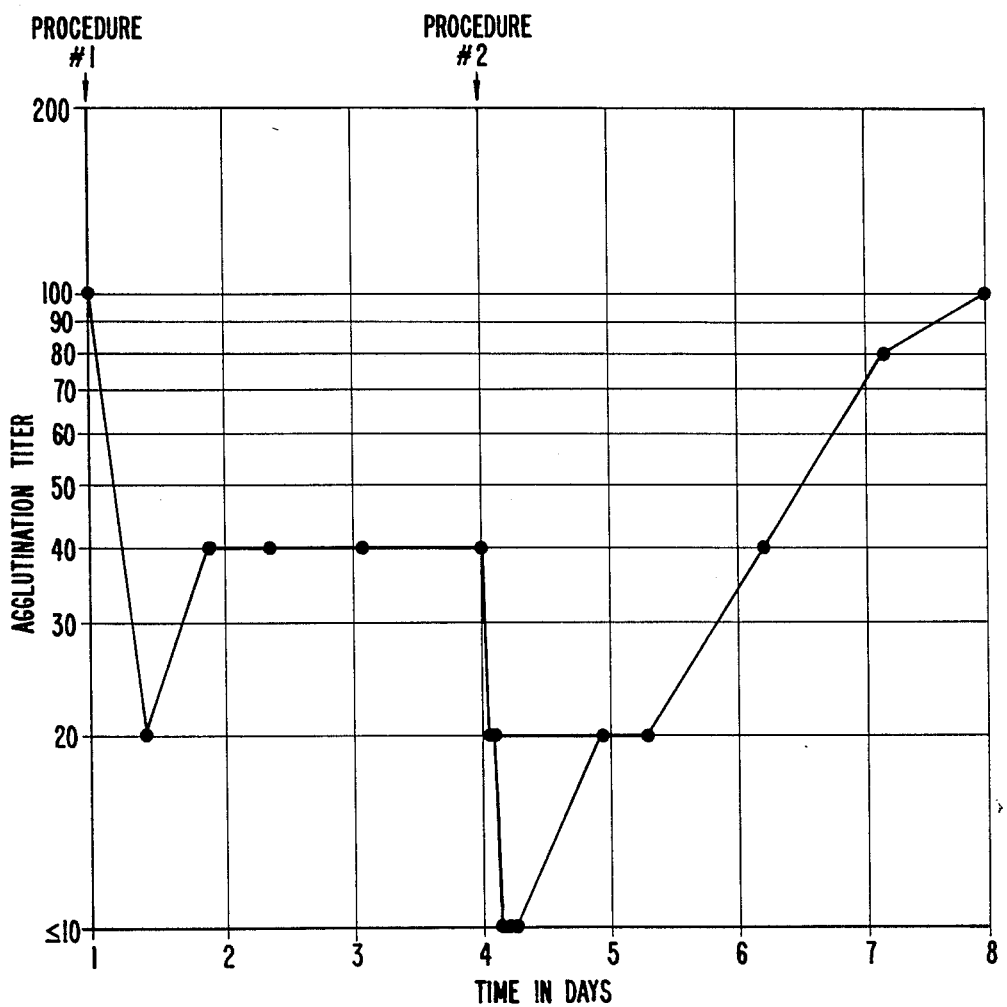
FIG._3.

METHODS AND COMPOSITIONS FOR TRANSIENT ELIMINATION OF HUMORAL IMMUNE ANTIBODIES

BACKGROUND OF THE INVENTION

1. Field of the Invention

The present invention relates generally to methods and compositions for facilitating the therapeutic or diagnostic administration of exogenous macromolecules to vertebrate hosts. In particular, it relates to methods and compositions for the extracorporeal removal of endogenous antibody elicited by human patients in response to treatment or diagnosis with exogenous antibodies.

Various immunotherapeutic strategies have been developed to mimic or bolster a patient's own immune response in fighting a disease or infection. In general, such immunotherapeutic strategies involve the administration of exogenous (non-human) antibody to the patient which are intended to react with a particular remainder of the cells unaffected. Usually, the antibody will be attached to a lethal agent, such as a drug, radioactive isotope, or a toxin, which will result in killing the cells without reliance on the patient's own humoral response mechanism. Alternatively, non-conjugated antibodies can be used with reliance on the patient's own immune system to kill the desired cells. The use of antibody conjugated to lethal agents, generally referred to as immunotoxins, has offered great hope in the treatment of cancers where the antibodies may be directed at tumor markers which differentiate the cancer cells from normal body cells.

Despite certain initial successes in cancer therapy, consistent effective treatments have not yet been achieved. One particular problem has been that the patient's immune system recognizes the exogenous antibodies as "foreign." Thus, initial treatments with the immunotoxins will sensitize the patient and subsequent treatments can evoke increasingly strong immune responses which can interfere with the effectiveness of the therapy. As it will usually be desirable to continue the therapy over relatively long periods of time, the immune response has proven to be a major impediment to effective treatment.

Various diagnostic strategies using radiolabeled antibodies have been developed to determine the size and position of various tissues within a patient's body. These diagnostic modalities include locating metastatic tumor foci, determining the size of heart tissue, evaluating vascular abnormalities, etc. These techniques have also been associated with the problem of the patient's endogenous immune reaction to the diagnostic macromolecules. As it will usually be desirable to repeat, at various times, the diagnostic procedure over relatively long periods, the immune response will be a major impediment to effective diagnosis.

It would thus be desirable to provide methods and compositions which will inhibit or minimize the patient's immune response to the administration of exogenous antibodies or other macromolecules. In particular, it would be desirable if such methods would allow the repeated administration of exogenous antibodies or macromolecules to an individual patient over extended periods of time, preferably indefinitely.

2. Description of the Background Art

Specific removal of circulating antibody by extracorporeal immunoadsorption employing specifically immobilized antigen has been described by various investigators. Specific removal of antibody from blood employing hemoperfusion through a porous gel was originally described by Schenkein et al. (1971) J. Clin. Invest. 50:1864. Terman and co-workers subsequently described techniques employing collodion-charcoal in which circulating antibody in animal plasma could be removed in an extracorporeal system as described in Clin. Exp. Immunol. (1976) 24:231 and Clin. Exp. Immunol. (1977) 28:180. This technique was successfully applied by Terman and co-workers to treat a patient with systemic lupus erythematosus as described in Lancet (1979) 2:824. However, it was later demonstrated by Balint et al., Cancer Res. (1984) 44:734, that such absorbents may leak the immobilized protein upon contact with blood plasma. Such leakage can cause further hyperimmunization of the host after the immunoadsorption procedure. Blood treatment systems for the removal of anti-A and anti-B antibodies are described by Bensinger et al. in a technique which utilizes synthetic human blood group antigens covalently linked to a silica matrix as described in N. Engl. J. Med. (1981) 304:160. The preparation and use of immunotoxins in the treatment of cancer and other diseases is taught in U.S. Pat. Nos. 4,340,535; 4,590,071; and 4,671,958. The extracorporeal removal of patient antibody produced in response to treatment with exogenous antibody has not been previously described. A system for the extracorporeal adsorption of IgG and circulating immune complexes using a protein A column is described in U.S. Pat. No. 4,681,870.

SUMMARY OF THE INVENTION

Methods and systems are provided for the extracorporeal removal of endogenous antibody produced in response to treatment of a vertebrate host, usually a human patient, with exogenous macromolecules, usually exogenous antibodies, more usually exogenous antibodies coupled to a cytotoxic agent. The exogenous antibody is administered to treat a disease characterized by the presence of a class of abnormal cells, such as neoplastic cancer cells. The exogenous macromolecules specifically interact with the abnormal cells in order to kill or otherwise inhibit the growth of these cells.

While the initial administration of the exogenous macromolecules will seldom result in an immediate interfering immune response, the patient will become sensitized to the exogenous macromolecules which acts as an antigen. Thus, second and subsequent administrations of the exogenous macromolecule will result in a more immediate and potent secondary humoral response which can interfere with the desired cytotoxic activity of the macromolecule.

In order to inhibit the secondary immune response, circulating antibody specific for the exogenous antibody is removed from the host. In particular, the levels of such antibody in circulation are reduced to near background titer levels as measured by any standard antibody titer assay technique. Such reduction, of course, must be maintained for a sufficient time to allow the injected immunotoxins to perform its function.

The circulating antibody may be extracorporeally removed using an immunoadsorbent column specific for the endogenous antibody. Blood from the patient is withdrawn either continuously or discontinuously, separated into its cellular components and plasma, and the plasma is perfused through the immunoadsorbent material in order to remove the antibody. The treated plasma and cellular components of the blood are then reinfused into the patient, either separately or simultaneously. Typically, plasma perfusion according to the present invention will be carried out immediately prior to the second and subsequent administrations of the exogenous macromolecules.

BRIEF DESCRIPTION OF THE DRAWINGS

FIG. 1 is an exploded view of an immunoadsorbent column suitable for use in the present invention.

FIG. 2 is a diagrammatic representation of a system for the extracorporeal treatment of blood suitable for use in the method of the present invention.

FIG. 3 illustrates the transient elimination of circulating antibody accomplished with the method of the present invention.

DESCRIPTION OF THE SPECIFIC EMBODIMENTS

The method of the present invention will be used in conjunction with the therapeutic or diagnostic administration of exogenous macromolecules to a vertebrate host, usually a human patient. The exogenous macromolecules will be administered to the host as part of a therapeutic or diagnostic regimen for a specific disease. It will usually be desirable to administer the exogenous macromolecules over an extended period of time, typically weeks, and more typically months. As the macromolecule is exogenous, the immune system of the host will recognize it as foreign or non-self, leading to an adverse immune response. After time, the patient will become sensitized to the exogenous macromolecules and the patient's own immune system will inhibit the activity of the macromolecules in treating the primary disease. The present invention provides a method for the extracorporeal removal of the endogenous antibody produced as part of the immune response to the administration of the exogenous macromolecules.

The exogenous macromolecules administered to the patient will usually be antibodies or other receptors specific for a class of abnormal cells within the patient, typically neoplastic cells characterized by marker antigens which allow the antibody to specifically bind the cell to the substantial exclusion of normal cells lacking the antigen. The antibody for human administration will typically be raised in a non-human host, such as a mouse, rat, sheep, goat, or other vertebrate capable of producing an immune response. Usually, monoclonal antibody will be produced by well known methods.

Once antibody specific for the cellular class has been produced, it will usually be coupled to a cytotoxic agent, such as a radioactive isotope, a natural toxin, such as a plant, animal, or bacterial toxin, or a cytotoxic drug, such as methotrexate adriamycin, fluorouracil, cerubidine, bleomycin, alkeran, valbon, oncovin and the like. Of particular interest is monoclonal antibody coupled to the A chain of certain toxic lectins, such as ricin and abrin. The monoclonal antibody, or portion thereof such as the $F_{ab}$ fragment, replaces the natural B chain of such toxic lectins which act as a non-specific receptor necessary for toxic activity. By replacing such a non-specific receptor with a receptor specific for the desired class of cells, the cytotoxicity of the toxin may be substantially limited to the desired cells.

The use of immunotoxins in human therapy is well known in the art and described in detail in U.S. Pat. Nos. 4,671,958; 4,590,071; and 4,340,535, the disclosures of which are incorporated herein by reference.

The method of the present invention relies on the specific removal of endogenous antibody produced as part of the immune response to the administration of exogenous (non-self) antibodies to the host being treated. Removal is accomplished using an immunoadsorbent having immobilized receptors specific for the endogenous antibody. The nature of the receptor is not critical so long as it is capable of being immobilized on a suitable matrix and thereafter binding the endogenous antibody. Conveniently, the receptor may be the exogenous antibody itself which will act as an antigen in the column capable of binding the endogenous antibody in the host's circulatory system. Alternatively, the column receptor may be antibody specific for the source of the administered exogenous antibody. For example, if mouse antibody is being administered to a human host, the receptor in the immunoadsorbent column could be anti-mouse antibody. Similarly, for sheep antibody, anti-sheep antibody could be used in the immunoadsorbent column. Anti-idiotypic antibody might also find use as the receptor.

A wide variety of materials will be suitable as the immunoadsorbent support matrix. Ideally, the matrix will be mechanically strong, sufficiently hydrophilic to avoid non-specific binding of proteins, and stable to blood and other aqueous solutions. The matrix should be porous to allow for easy diffusion of large protein molecules. Suitable matrix materials include polysaccharides, polyamides, glass beads, particulate silica, and the like. Particularly preferred are particulate silicas, including microcrystalline silicas, such as diatomites; crystalline silicas, such as quartz; and organic polymers of suitable inertness and chemical characteristics. The silica or other inert particulate beads should have a particle size in the range from about 30 to 120 mesh, usually in the range from about 45 to 60 mesh.

In the preferred embodiment, the solid-phase matrix of the immunoadsorbent of the present invention will be formed from non-polymeric diatomite aggregates. Usually, the diatomite material will be calcined to removed any remaining organic material and to harden the surface of the aggregates in order to lessen breakage and degradation of the immunoadsorbent during use. The diatomite material will consist of silica (silicon dioxide) with lesser amounts of other minerals, including aluminum oxide, calcium oxide, magnesium oxide, ferric oxide, and the like. Usually the diatomite material will comprise at least 80% silica, with less than 5% by weight of any other mineral. Other impurities may be present in the diatomite, but care should be taken that such impurities are not toxic and non-degradative to the biological fluid being treated. A particularly suitable solid-phase silica (diatomite) matrix may be obtained from Johns-Manville Corporation under the tradename Chromosorb ®.

An exemplary immunoadsorbent material comprising mouse monoclonal IgG covalently coupled to a solid-phase silica (diatomite) matrix may be prepared as follows.

Monoclonal mouse IgG for use in the immunoadsorbent material is purified from culture fluids employing a series of known techniques. The culture fluid containing the mouse IgG is treated with 50% ammonium sulfate to precipitate the mouse IgG from the fluid phase. The precipitated mouse IgG is collected by centrifugation and dissolved in a solution containing 0.025 Molar phosphate buffer, pH 7.50. The solution is then dialyzed extensively with several changes of 0.025 Molar phosphate buffer, pH 7.50, to remove the excess ammonium sulfate from the solution, and then applied to a DEAE ion exchange column that has been equilibrated with water that has been subjected to reverse osmosis and deionization. The purified mouse monoclonal IgG is then eluted from the column employing a solution containing 0.025 Molar phosphate buffer, pH 7.50. Typically the final purity of the product is 90-99%.

The mouse monoclonal IgG is covalently coupled to the solid surface of the silica matrix by derivatizing the material to introduce active functional groups and reacting the derivatized matrix with a coupling agent under chemical conditions which binds the mouse IgG to the matrix.

Amino groups may be introduced to the silica matrix as the active functional group by any suitable method. For example, the silica matrix is first acid washed and extensively washed with pyrogen free water. The acid washed silica is then reacted in a 5% to 10% solution of aminosilane, such as λ-aminopropyltriethoxysilane or N'-(β-aminoethyl)-N-(β-aminoethyl)-λ-aminopropyltrimethoxysilane with the pH adjusted to 3.0 to 4.0. After 2 hours at about 75° C., the matrix is extensively washed with pyrogen free water and incubated overnight at 100° C.

Once the silica matrix has been derivatized with amino groups, the mouse monoclonal IgG is introduced by reaction with a carbodiimide which forms a covalent link between the matrix and the mouse IgG. The carbodiimide will have the formula

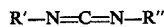

where R' and R" may be the same or different. The preferred carbodiimide is 1-cyclohexyl-3-(2-morpholinoethyl) carbodiimide metho-p-toluenesulfonate.

The binding reaction for the amino-derivatized matrix is carried out under the following conditions. The mouse IgG is extensively dialyzed against a solution of phosphate buffer, pH 4.75. The carbodiimide is dissolved separately in pyrogen free water. The dialyzed mouse IgG and the dissolved carbodiimide are then mixed with the derivatized silica matrix and the pH is rapidly adjusted to 4.75. The materials are gently mixed or an extended period, usually about 4 to 24 hours at 25° C. The matrix is then extensively washed with pyrogen free water and then acid washed at a pH from about 2.0 to 2.5 to remove non-covalently bound mouse IgG from the immunoadsorbent matrix. The material is then finally washed, dried, and checked for the presence of pyrogens.

Referring now to FIG. 1, the construction of a suitable cartridge 10 for containing the immunoadsorbent matrix as just described is illustrated. The cartridge comprises a cylinder 12, a pair of retaining screens 14, and a pair of end caps 16. The end caps 16 each include a flange element 18 projecting from one surface thereof and a connector nipple 20 projecting from the other surface thereof. The connector nipple includes an axial passage 22 therethrough to define inlet/outlet ports through the end caps 16.

The cylinder 12 includes an annular groove 26 at each end thereof. The flange element 18 on each end cap includes a mating ring 28 on the inner cylindrical surface thereof, which mating ring engages the annular groove 26 when the caps are placed over the end of the cylinder 12. Each screen 14 includes a gasket 30 around its circumference, which gasket serves as a sealing member between the end cap 16 and the cylinder 12 when the cartridge 10 is assembled. To assemble the cartridge 10, a first screen 14 is placed over one end of the cylinder 12, and an end cap 16 is fitted over the screen 14. The cylinder 1 is then filled with the immunoadsorbent matrix and assembly of the cartridge completed by placing the remaining screen 14 and end cap 16 in place.

The dimensions of the cartridge 10 are not critical and will depend on the desired volume of immunoadsorbent matrix. The volume of the cylinder !2 will typically range from about 250 to 500 cc, having a diameter in the range from about 6 to 8 cm and a length in the range from about 8 to 12 cm.

The column (FIG. 2) which comprises a cartridge 10 containing a suitable amount of the immunoadsorbent matrix prepared as described above, may be sterilized, and either used immediately or sealed and stored for later use.

Prior to use, the column 11 will be washed with normal saline followed by a wash with normal saline containing heparin or other suitable anti-coagulants such as anti-coagulant citrate dextrose (ACD). The column 11 may then be connected to a cell separator 40 (FIG. 2) to receive separated plasma therefrom. The cell separator 40 may be a continuous flow cell separator such as an IBM Model 2997 or may comprise a semi-permeable membrane which allows passage of the plasma and blood proteins but prevents passage of cellular elements of the blood. In the case of a semi-permeable membrane, a blood pump 42 will be required to pass the blood through the membrane. Suitable pumps include a tube and peristaltic pumps where the blood is isolated from the pumping machinery to prevent contamination. The blood will pass through the cell separator 40 at a rate in the range from about 20 to 30 ml/minute typically until a total volume of blood plasma has been processed. The blood cells are mixed with the plasma passing from the treatment column 11, and the recombined blood returned to the patient. Typically, a microfilter 44 is provided at the outlet of the treatment column 11 to prevent passage of macroscopic particles which might be lost from column 11.

The immunoadsorbent column and system just described are used for the extracorporeal treatment of blood from patients undergoing treatment with exogenous macromolecules, typically immunotoxins in cancer therapy. The exogenous macromolecules are typically administered by intravenous injection, although subcutaneous and intraperitoneal injection would also be possible. Patients initially treated with the immunotoxins will usually not show an immediate adverse immune response. It is only after the patient has become sensitized by the production of memory B cells that the further treatment with the immunotoxins will elicit an immediate and adverse immune response. The immune response includes the rapid expansion of B memory cells into antibody-producing B cell clones producing large quantities of antibody specific for the immunotoxin. Binding of the antibody to the immunotoxin interferes substantially with the desired cytotoxic activity of the immunotoxins for the target abnormal cells.

The method of the present invention is used to reduce the presence of the anti-immunotoxin antibodies in circulating blood plasma.

Extracorporeal treatment of blood plasma according to the present invention may be performed at any time during the interval between one injection with the immunotoxin and prior to the next injection with the same immunotoxin. Ideally, the extracorporeal treatment to remove antibody will be made immediately prior to each administration of the immunotoxin.

The extracorporeal blood perfusion may be performed continuously using the system illustrated in FIG. 2. Alternatively, discrete volumes of blood may be removed from the patient, treated as described above, and the treated plasma and cellular components of the blood returned to the patient after the treatment is complete. In either case, it is necessary that sufficient amounts of the endogenous antibody must be removed to inhibit or reduce the interference of the antibody with the newly administered exogenous macromolecule, e.g., immunotoxin. Sufficient amounts of antibody are removed such that the circulating levels of the antibody are eliminated or reduced to near background titer levels as measured by any standard antibody titer assay technique. The reduction is accomplished and maintained for a sufficient time to allow the injected immunotoxin to perform its function.

The following examples are offered by way of illustration, and not by way of limitation.

EXPERIMENTAL

Materials and Methods

1. Preparation of Immunoadsorbent Material

Acid washed silica matrix (Chromosorb®P, No. C5889, Johns Manville 1.25 Kilograms) was weighed out, divided into 4 parts, and added to 4 Fernback type flasks. The matrix was re-hydrated with water and vigorously shaken overnight in a gyrotory shaker at approximately 150 rpm. This procedure appeared to make silica particles which generated few fines in later handling procedures. After washing, the silica matrix was added to an approximately 5–10% solution of appropriate silane, incubated for 2 hours at 70°–80° C., extensively washed with water, and incubated at 115° C. until dry.

The dried silanized silica matrix (120 grams) was re-hydrated and extensively washed with water to remove generated fines. The silica matrix was then mixed with 318.75 milligrams of mouse IgG in 0.025 Molar phosphate buffer, pH 4.75. Fifteen grams of carbodiimide were dissolved in water and then added to the silica-mouse IgG. The pH of the solution was checked and adjusted if necessary to insure that the final pH was 4.75 ±0.15. The mixture was gently rotated in a roller apparatus for 22 hours at 25° C. The matrix was then extensively washed with water and the uptake of the mouse IgG was determined. After the last wash, as much water as possible was decanted from the matrix. Acid water, pH 2.5, was added to the matrix and the mixture was gently rotated for 5 minutes at 5° C. The amount of mouse IgG released from the matrix after this procedure was then determined. The matrix was extensively washed with water and stored in a sterile condition. The results were as follows:

Bound IgG: 305.70 mg
IgG Released: 15.75 mg
IgG/gm adsorbent: 2.90 mg/gm

2. Therapeutic Use of Column to Remove Circulating Antibody to Mouse IgG

To demonstrate the clinical utility of the immunoadsorption column, sheep were immunized with mouse IgG to develop circulating antibodies to the extraneous antigen. Circulating antibody titers were measured employing a hemagglutin assay with sheep red blood cells coated with mouse IgG as described (Handbook of Exper. Immunol., Vol. 1). This animal model was then employed as a study system which would be encountered in an experimental clinical setting.

The extracorporeal immunoadsorption procedures were performed in sheep after surgery to implant indwelling catheters for vascular blood access. Two Fenwall pumps were used in conjunction with a F.D.A. approved Asahi hollow fiber unit to separate anticoagulated blood into cellular components and plasma. The cellular components were returned unprocessed. The plasma was perfused over a column containing approximately 320 mg mouse IgG covalently bound to silica as described above and the treated plasma was returned to the animal. Mouse IgG was purified employing standard chromatographic procedures as described (Handbook of Exper. Immunol , Vol. 1). The IgG purity was determined by polyacrylamide gel electrophoresis. The IgG was covalently coupled to silica, loaded into a biocompatible cartridge, and washed extensively with sterile water. Studies revealed that extensive washing of the column with 4–8 liters of sterile, pyrogen free water, immediately prior to use resulted in a lack of detectable pyrogens (Associates of Cape Cod, Woods Hole, MA). Plasma flow rates were between 20–25 ml/min. Four columns were employed for each procedure. For each column used, 1500 ml of plasma were passed over each column. Two procedures (employing 4 columns for each procedure) were performed over a 4 day period, one procedure on the first day and a final procedure on the 4th day. In addition, for each column used, the first 250 ml processed were allowed to incubate in the column for 30 minutes prior to re-entry into the animal to allow any complement generated anaphylatoxins to spontaneously degrade.

No major complications occurred during the treatments. A febrile response characterized by the development of a fever did occur. The immunoadsorption column treatments were tolerated and were clinically manageable.

Analysis of plasma samples immediately after passage through the immunoadsorbent column revealed that there was a lack of detectable antibody in the hemagglutination assay described above. Pre-column treatment antibody was present in the plasma as demonstrated by a titer of 1/100 in the hemagglutination assay. This showed that the immunoadsorbent column was effectively binding anti-mouse IgG antibody present in circulating sheep plasma.

Analysis of circulating plasma samples taken from the sheep approximately 1 hour after the immunoadsorption procedure revealed a substantial reduction in circulatin antibody levels. As shown in FIG. 3, at the end of the second immunoadsorption procedure on day 4, the antibody level was transiently eliminated from circulating plasma. This data demonstrated the effectiveness and clinical utility of the immunoadsorbent columns.

After each procedure, the immunoadsorbent columns were extensively washed with a buffer solution at pH 7.5 to remove unbound proteins. Bound proteins were removed from the columns by elution with an acid buffer at pH 2.5. Immediately after elution, the pH of the acid buffer containing the eluted proteins was adjusted to 7.5. Analysis of the eluted proteins by polyacrylamide gel electrophoresis revealed the presence of predominantly sheep IgG antibody. This indicates that sheep antibody was binding to the mouse IgG antigen covalently coupled to the immunoadsorbent matrix. Determination of the total protein bound to all 4 columns used in each procedure revealed that 800–900 mgs of circulating sheep antibody were removed from circulation in each procedure.

Although the foregoing invention has been described in some detail by way of illustration and example for purposes of clarity of understanding, it will be obvious that certain changes and modifications may be practiced within the scope of the appended claims.

What is claimed is:

1. A method for inhibiting sensitivity in a vertebrate host undergoing therapeutic or diagnostic administration of exogenous macromolecules, said method comprising the extracorporeal removal from the patient of endogenous antibodies produced in response to the administration of the exogenous macromolecules.

2. A method as in claim 1, wherein the removal of the endogenous antibodies is effected by passage of patient plasma through an immunoadsorbent having immobilized receptor specific for the endogenous antibody.

3. A method as in claim 2, wherein the receptor is the exogenous macromolecule itself.

4. A method as in claim 2, wherein the immunoadsorbent comprises receptor covalently bound to a physiologically inert matrix.

5. A method as in claim 4, wherein the physiologically inert matrix is silica.

6. A method as in claim 1, wherein endogenous antibody levels are reduced to about background titer levels or below immediately prior to the administration of additional exogenous antibody.

7. In a method for administering to a vertebrate host multiple doses of exogenous antibodies at preselected intervals between successive doses, the improvement comprising inhibiting immune sensitivity to such exogenous antibodies by the extracorporeal removal from the patient of endogenous antibodies produced in response to the administration of the exogenous antibodies.

8. A method as in claim 7, wherein the endogenous antibodies are removed immediately prior to administration of a dose of the exogenous antibodies.

9. A method as in claim 8, wherein the endogenous antibody levels are reduced to about background titer levels or below.

10. A method as in claim 7, wherein the exogenous antibodies are coupled to a cytotoxic agent.

11. A method as in claim 7, wherein the removal of the endogenous antibodies is effected by passage of patient plasma through an immunoadsorbent having immobilized receptor specific for the endogenous antibody.

12. A method as in claim 11, wherein the receptor is the exogenous antibody itself.

13. A method as in claim 11, wherein the immunoadsorbent comprises receptor covalently bound to a physiologically inert matrix.

14. A method as in claim 13, wherein the physiologically inert matrix is silica.

15. A method for treating a vertebrate host with exogenous antibodies, said method comprising the following steps:
    (a) removing blood from a patient who has previously been injected with exogenous antibodies which have in response produced endogenous antibodies;
    (b) separating the removed blood into cellular components and plasma;
    (c) contacting the plasma with an immunoadsorbent specific for the endogenous antibodies;
    (d) reinfusing the cellular components and the treated plasma into the patient; and
    (e) administering exogenous antibodies to the patient.

16. A method as in claim 15, wherein steps (a) through (d) are performed and completed immediately prior to step (e).

17. A method as in claim 15, wherein the exogenous antibodies are specific for a class of abnormal cells within the patient.

18. A method as in claim 17, wherein the abnormal cells are neoplastic cells.

19. A method as in claim 15, wherein the exogenous antibodies are specific for a class of normal cells within the patient.

20. A method as in claim 19, wherein the normal cells are being evaluated to determine the size and position of a particular tissue.

21. A method as in claim 19, wherein the normal cells are heart muscle and vascular tissue.

22. A method as in claim 15, wherein the removal of the endogenous antibodies is effected by passage of patient plasma through an immunoadsorbent having immobilized receptor specific for the endogenous antibody.

23. A method as in claim 15, wherein the immunoadsorbent comprises a receptor specific for the exogenous antibody coupled to a physiologically inert matrix.

24. A method as in claim 23, wherein the receptor is the exogenous antibody itself.

25. A method as in claim 23, wherein the physiologically inert matrix is silica.

* * * * *